(12) United States Patent
Kim

(10) Patent No.: US 9,401,040 B2
(45) Date of Patent: Jul. 26, 2016

(54) IMAGE PROCESSING APPARATUS AND IMAGING PROCESSING METHOD

(71) Applicant: SAMSUNG ELECTRONICS CO., LTD., Suwon-si (KR)

(72) Inventor: Yun Tae Kim, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 183 days.

(21) Appl. No.: 14/336,269

(22) Filed: Jul. 21, 2014

(65) Prior Publication Data

US 2015/0071516 A1 Mar. 12, 2015

(30) Foreign Application Priority Data

Sep. 10, 2013 (KR) .......................... 10-2013-0108453

(51) Int. Cl.
| | |
|---|---|
| *G06T 15/00* | (2011.01) |
| *G06T 15/08* | (2011.01) |
| *A61B 8/08* | (2006.01) |
| *G01S 15/89* | (2006.01) |
| *G01S 7/52* | (2006.01) |
| *A61B 8/00* | (2006.01) |
| *G10K 11/34* | (2006.01) |

(52) U.S. Cl.
CPC ............... *G06T 15/08* (2013.01); *A61B 8/0866* (2013.01); *A61B 8/466* (2013.01); *A61B 8/5207* (2013.01); *G01S 7/5202* (2013.01); *G01S 7/52025* (2013.01); *G01S 7/52071* (2013.01); *G01S 15/8993* (2013.01); *A61B 8/4405* (2013.01); *A61B 8/4411* (2013.01); *G01S 15/8915* (2013.01); *G10K 11/346* (2013.01)

(58) Field of Classification Search
CPC ......... G06T 15/00; G06T 15/06; G06T 15/08; G06T 15/50; A61B 6/5223; A61B 8/483; A61B 8/523
See application file for complete search history.

(56) References Cited

U.S. PATENT DOCUMENTS

| | | | |
|---|---|---|---|
| 6,999,078 B1 | 2/2006 | Akerman et al. | ............ 345/424 |
| 2008/0297509 A1* | 12/2008 | Matsumoto | .................. 345/424 |
| 2012/0127200 A1* | 5/2012 | Kohara et al. | ................. 345/629 |

FOREIGN PATENT DOCUMENTS

| | | | | |
|---|---|---|---|---|
| JP | 11-290318 A | 10/1999 | ............... | A61B 8/00 |
| KR | 10-2011-0022445 A | 3/2011 | ............... | A61B 8/00 |
| KR | 10-1253608 B1 | 4/2013 | ............... | A61B 8/00 |

* cited by examiner

*Primary Examiner* — Andrew W Johns
(74) *Attorney, Agent, or Firm* — Sughrue Mion, PLLC

(57) ABSTRACT

Disclosed herein are an imaging processing apparatus for representing an object realistically, and an imaging processing method thereof. The image processing apparatus includes: a volume data generator configured to generate volume data of an object; a volume renderer configured to project the volume data to a first plane with respect to a user's viewpoint, and to acquire a projection image, wherein the volume renderer determines a value of each pixel of the projection image based on respective distances between first surface points and second surface points, the first surface points being points that are shown from the user's viewpoint from among points constituting a surface of the volume data, the second surface points being points that are shown from a position of virtual light from among the points constituting the surface of the volume data.

15 Claims, 14 Drawing Sheets
(3 of 14 Drawing Sheet(s) Filed in Color)

IMAGE PROCESSING APPARATUS AND IMAGING PROCESSING METHOD

CROSS-REFERENCE TO RELATED APPLICATION

This application claims priority from Korean Patent Application No. 10-2013-0108453, filed on Sep. 10, 2013 in the Korean Intellectual Property Office, the disclosure of which is incorporated herein by reference in its entirety.

BACKGROUND

1. Field

Exemplary embodiments relate to an imaging processing apparatus for representing an object realistically, and an imaging processing method thereof.

2. Description of the Related Art

With growing interest in health, studies which relate to medical imaging apparatuses are actively being conducted. Medical imaging apparatuses include an X-ray imaging apparatus, a fluoroscopy system, a Computerized Tomography (CT) scanner, a Magnetic Resonance Image (MRI) apparatus, a Positron Emission Tomography (PET) apparatus, and an ultrasonic imaging apparatus.

The medical imaging apparatuses display a two-dimensional (2D) medical image or a three-dimensional (3D) medical image of an object. The 2D medical image is a section image of the inner tissue of an object. The 3D medical image is an image which is obtained by performing volume rendering on 3D volume data which is generated based on a plurality of section images.

The 2D and 3D medical images may be black-and-white images or color images. Recently, color images are primarily used, since black-and-white images have a limitation in realistic expression. A color image of the inner tissue of an object can be produced by mapping colors which are similar to actual colors of the inner tissue to a black-and-white image of the object.

SUMMARY

Therefore, it is an aspect of one or more exemplary embodiments to provide an image processing apparatus for representing an object realistically, and an image processing method thereof.

Additional aspects of the exemplary embodiments will be set forth in part in the description which follows and, in part, will be obvious from the description, or may be learned by practice of the exemplary embodiments.

In accordance with one aspect of one or more exemplary embodiments, an image processing apparatus includes: a volume data generator configured to generate volume data which relates to an object; a volume renderer configured to project the volume data to a first plane with respect to a viewpoint of a user, and to acquire a projection image, wherein the volume renderer is further configured to determine a value of each pixel of the projection image based on respective distances between first surface points and second surface points, the first surface points being points that are shown from the viewpoint of the user from among points which constitute a surface of the volume data, the second surface points being points that are shown from a position of virtual light from among the points which constitute the surface of the volume data.

In accordance with another aspect of one or more exemplary embodiments, an image processing method includes: generating volume data which relates to an object; and projecting the volume data to a first plane with respect to a viewpoint of a user, and acquiring a projection image, wherein the acquiring the projection image comprises determining a value of each pixel of the projection image based on respective distances between first surface points and second surface points, the first surface points being points that are shown from the viewpoint of the user from among points which constitute a surface of the volume data, the second surface points being points that are shown from a position of virtual light from among the points which constitute the surface of the volume data.

Therefore, by giving a translucent effect using virtual light upon volume rendering of volume data, a more realistic image of an object or of the inner tissue of an object can be produced.

Accordingly, a user's satisfaction with images can be improved.

BRIEF DESCRIPTION OF THE DRAWINGS

The patent or application file contains at least one drawing executed in color. Copies of this patent or patent application publication with color drawing(s) will be provided by the Office upon request and payment of the necessary fee. These and/or other aspects will become apparent and more readily appreciated from the following description of exemplary embodiments, taken in conjunction with the accompanying drawings of which.

DETAILED DESCRIPTION

Figure 1:
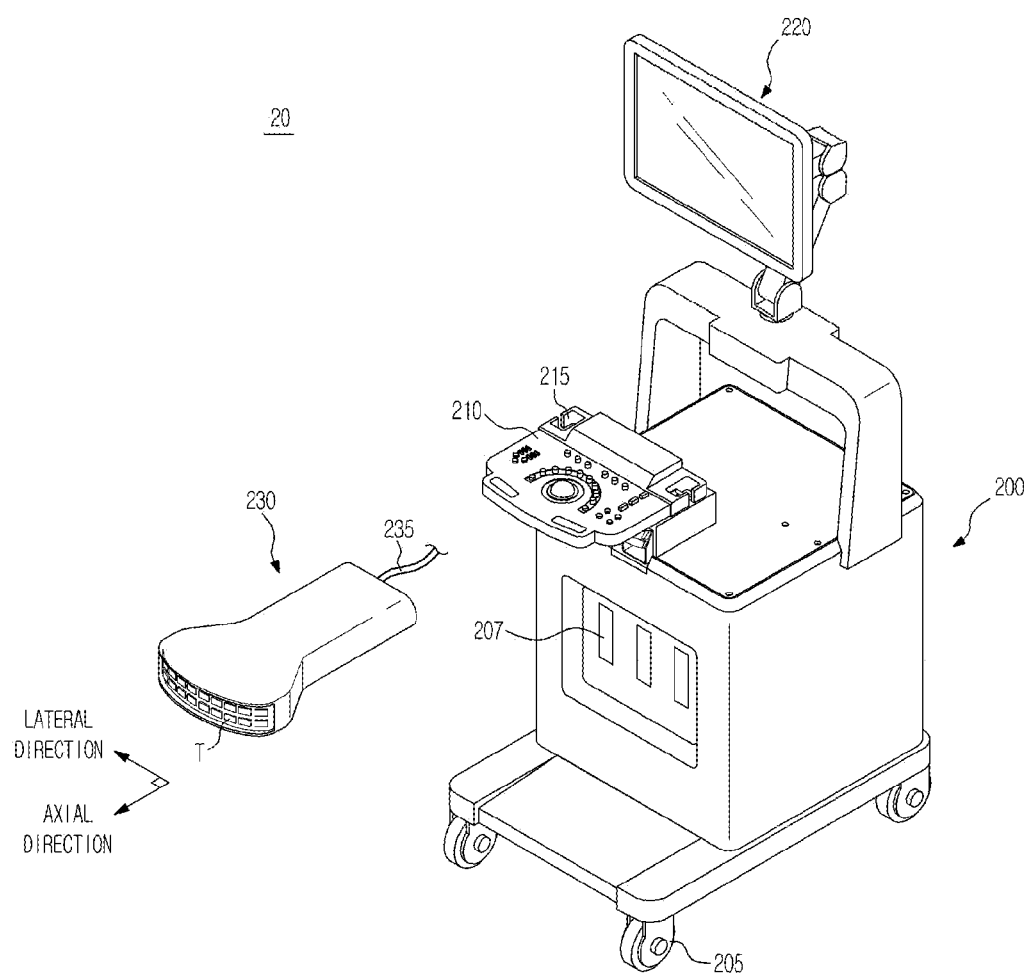
FIG. 1 is a perspective view of an ultrasonic imaging apparatus, according to an exemplary embodiment.

Reference will now be made in detail to exemplary embodiments, examples of which are illustrated in the accompanying drawings, wherein like reference numerals refer to like elements throughout.

In the following description, an image processing apparatus may be a medical imaging apparatus. Medical imaging apparatuses include an X-ray imaging apparatus, a fluoroscopy system, a Computerized Tomography (CT) scanner, a Magnetic Resonance Image (MRI) apparatus, a Positron Emission Tomography (PET) apparatus, and an ultrasonic imaging apparatus. However, the medical imaging apparatus is not limited to the above-mentioned apparatuses, and may be any other medical equipment capable of creating three-dimensional (3D) volume data from a plurality of section images or a plurality of projection images of the inner tissue of an object. In the following description, for convenience of description, the imaging processing apparatus is assumed to be an ultrasonic imaging apparatus.

The ultrasonic imaging apparatus irradiates ultrasonic waves toward a target inside an object, and receives information of ultrasonic waves (that is, ultrasonic echo) which are reflected from the target so as to non-invasively acquire section images which relate to soft tissue of the object or images which relate to blood vessels of the object based on the ultrasonic echo.

The ultrasonic imaging apparatus has advantages that it is a compact, low-priced apparatus as compared with other medical imaging apparatuses, such an X-ray imaging apparatus, a CT scanner, a MRI apparatus, and a nuclear medicine diagnosis apparatus, and the ultrasonic imaging apparatus can display images in real time. Also, the ultrasonic imaging apparatus has high safety, because there is no risk for patients to be exposed to radiation such as X-rays. As a result of these advantages, the ultrasonic imaging apparatus is widely used to diagnose the heart, breasts, abdomen, urinary organs, uterus, and/or other body parts.

FIG. 1 is a perspective view of an ultrasonic imaging apparatus, according to an exemplary embodiment.

Referring to FIG. 1, an ultrasonic imaging apparatus 20 may include a main body 200, an input unit (also referred to herein as an "input device") 210, a display unit (also referred to herein as a "display device" and/or as a "display") 220, and a probe 230.

The main body 200 may accommodate main components of the ultrasonic imaging apparatus 20. For example, referring to FIG. 2, the main body 200 may accommodate a controller 240, a transmit beamformer 250, a receive beamformer 260, an image processor 270, and a storage unit (also referred to herein as a "storage device" and/or as a "storage") 280. The individual components will be described in more detail with reference to FIG. 2 below.

In one side of the main body 200, one or more female connectors 207 may be provided. A male connector (not shown) may be physically coupled with one of the female connectors 207. The male connector may be connected to one end of a cable 235, and the other end of the cable 235 may be connected to the probe 230.

In the lower part of the main body 200, a plurality of castors 205 configured for moving the ultrasonic imaging apparatus 20 are provided. The castors 205 can fix the ultrasonic imaging apparatus 20 at a specific location, or move the ultrasonic imaging apparatus 20 in a specific direction.

The input unit 210 enables a user to input an instruction or a command for manipulating the ultrasonic imaging apparatus 20. For example, the user may input a diagnosis start command, a command for selecting an area to be diagnosed, a command for selecting a diagnosis type, and/or a command for selecting a mode for an ultrasonic image to be finally output, via the input unit 210. Modes for ultrasonic images may include an Amplitude mode (A-mode), a Brightness mode (B-mode), a Doppler mode (D-mode), an Elastography mode (E-mode), and a motion mode (M-mode). In addition, the user may input information which relates to a position of a user's viewpoint and a position of virtual light via the input unit 210.

The input unit 210 may include at least one of a keyboard, a mouse, a touch screen, a foot switch, and a foot pedal.

For example, the keyboard may be implemented as a hardware component, and mounted on the upper part of the main body 200. The keyboard may include at least one(s) of a switch(s), a key(s), a wheel, a joystick, a trackball, and a knop. As another example, the keyboard may be implemented as software, such as a Graphic User Interface (GUI). A keyboard which is implemented as software may be displayed via the display unit 220.

The foot switch or the foot pedal may be disposed below the main body 200. The user may control one or more functions of the ultrasonic imaging apparatus 20 by using the foot pedal.

In one side of the input unit 210, one or more probe holders 215 for holding the probe 230 may be provided. In FIG. 1, a case in which two probe holders 215 having the same size are provided around the input unit 210 is shown. However, the probe holders 215 may have different sizes and/or shapes, the number of the probe holders 215 is not limited to two, and the probe holders 215 may be provided at different locations. For example, the probe holders 215 may be provided in one side of the main body 200, and the number of the probe holders 215 may be one or more. When a plurality of probe holders 215 are provided, the probe holders 210 may have different shapes and sizes.

The display unit 220 may display ultrasonic images. More specifically, the display unit 220 may display ultrasonic images corresponding to a mode selected by a user. The display unit 220 may include at least one display.

The at least one display may have only a display function or may have both a display function and an input function. If the display is a touch screen, the display may have both a display function and an input function.

The at least one display may be separated from the main body 200. In this case, images produced by the ultrasonic imaging apparatus 20 may be transmitted to the at least one display via wired/wireless communication technologies.

Figure 2:
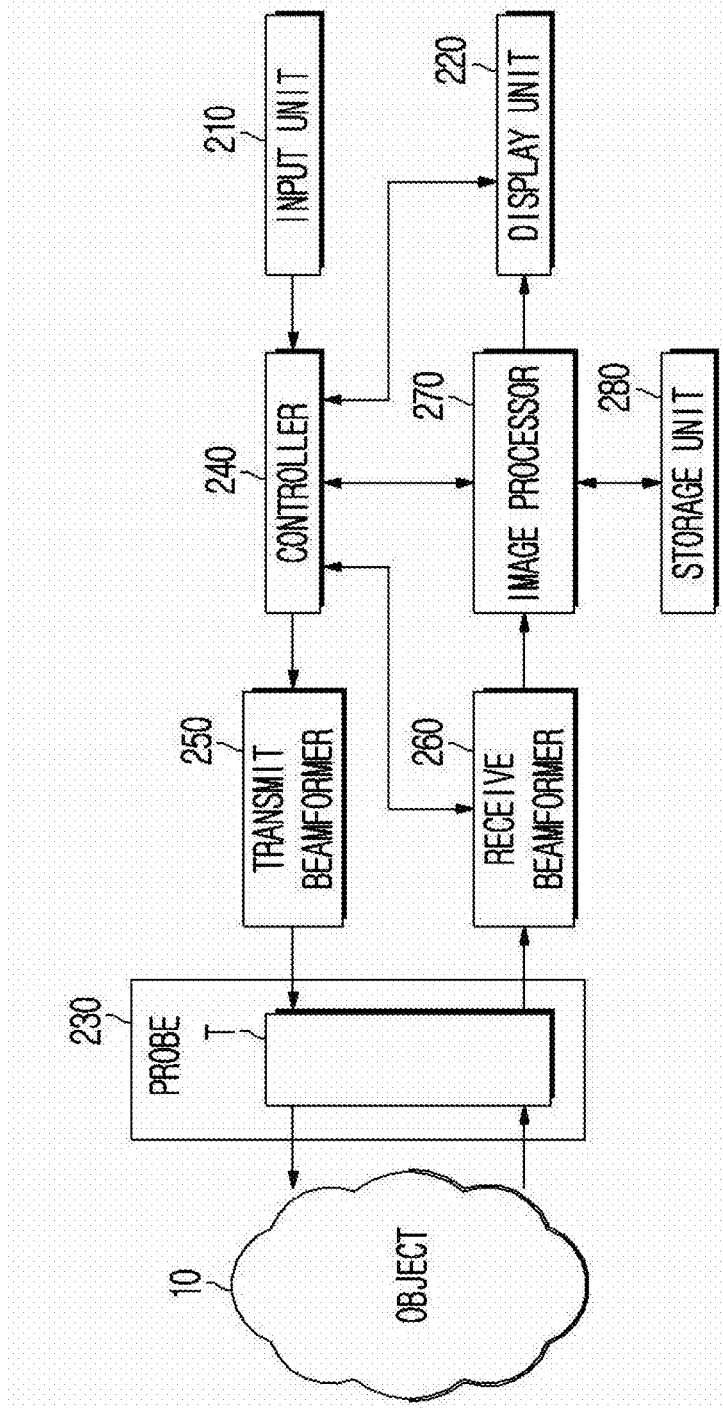
FIG. 2 is a block diagram of an ultrasonic imaging apparatus, according to an exemplary embodiment.

The probe 230 contacts the skin surface of an object 10 (see FIG. 2). One or more ultrasonic elements T are installed in one end of the probe 230. The ultrasonic elements T irradiate ultrasonic waves toward a target inside the object 10, receive at least one ultrasonic echo reflected from the target, and convert the at least one ultrasonic echo into at least one electrical signal. For example, each ultrasonic element T may include an ultrasonic generator configured to generate ultrasonic waves and an ultrasonic reception device configured to receive at least one ultrasonic echo and convert the at least one ultrasonic echo into at least one electrical signal. As another example, the ultrasonic element T itself may generate ultrasonic waves and receive at least one ultrasonic echo.

The ultrasonic elements T may be ultrasonic transducers. A transducer is a device of converting a specific type of energy into another type of energy. For example, the ultrasonic transducer may convert electricity energy into wave energy, or wave energy into electricity energy. In particular, the ultrasonic transducers T may perform all functions of an ultrasonic generator and an ultrasonic receiver.

In more detail, the ultrasonic transducers T may include a piezoelectric material and/or a piezoelectric thin film. If alternating current power from an external power supply or from an internal power storage unit, such as, for example, a battery, is applied to the piezoelectric material or the piezoelectric thin film, the piezoelectric material or the piezoelectric thin film vibrates at a specific frequency so that a specific frequency of ultrasonic waves are generated according to the vibration frequency. Meanwhile, if ultrasonic echo having a specific frequency arrives at the piezoelectric material or the piezoelectric thin film, the piezoelectric material or the piezoelectric thin film vibrates according to the frequency of the ultrasonic echo. At this time, the piezoelectric material or the piezoelectric thin film outputs alternating current corresponding to the vibration frequency.

Each ultrasonic transducer T may be a magnetostrictive ultrasonic transducer using the magnetostrictive effect of a magnetic material, a piezoelectric ultrasonic transducer using the piezoelectric effect of a piezoelectric material, or a capacitive micromachined ultrasonic transducer (CMUT) that transmits and receives ultrasonic waves using vibration of several hundreds or thousands of micromachined thin films. However, the ultrasonic transducer T may be any other type ultrasonic transducer capable of generating ultrasonic waves according to electrical signals or generating electrical signals according to ultrasonic waves.

The ultrasonic transducers T may be arranged in a linear array or in a convex array at the end part of the probe 230. In this case, the ultrasonic transducers T may be arranged in a line or in a matrix form. If the ultrasonic transducers T are arranged in a line, by moving the probe 230 in a scan direction, a plurality of ultrasonic images may be acquired. If the ultrasonic transducers are arranged in a matrix form, by transmitting ultrasonic waves at once, a plurality of ultrasonic images may be acquired.

Although not shown in the drawings, a cover for covering the ultrasonic transducers T may be provided.

FIG. 2 is a block diagram of an ultrasonic imaging apparatus, according to an exemplary embodiment.

Referring to FIG. 2, an ultrasonic imaging apparatus 20 may include an input unit 210, a display unit 220, a probe 230, a controller 240, a transmit beamformer 250, a receive beamformer 260, an image processor 270, and a storage unit 280.

The input unit 210, the display unit 220, and the probe 230 have been described above with reference to FIG. 1, and accordingly, further descriptions thereof will be omitted.

The controller 240 may control overall operations of the ultrasonic imaging apparatus 20. In detail, the controller 240 may generate a control signal for controlling at least one of the transmit beamformer 250, the receive beamformer 260, the image processor 270, and the display unit 220, according to an instruction or command received via the input unit 210. Also, the controller 240 may generate a control signal for controlling individual components according to an instruction or a command received from an external device via wired/wireless communication. In this case, the ultrasonic imaging apparatus 20 may include a communication unit, such as, for example, a transceiver, to receive the instruction or command from the external device.

The transmit beamformer 250 may perform transmit beamforming. The transmit beamforming is performed in order to focus ultrasonic waves from one or more ultrasonic elements T onto a focal point. That is, the transmit beamforming causes the ultrasonic elements T to generate ultrasonic waves in an appropriate order in order to compensate for time differences with which ultrasonic waves generated from the ultrasonic elements T arrive at the focal point. The transmit beamforming will be described in more detail with reference to FIG. 3, below.

Figure 3:
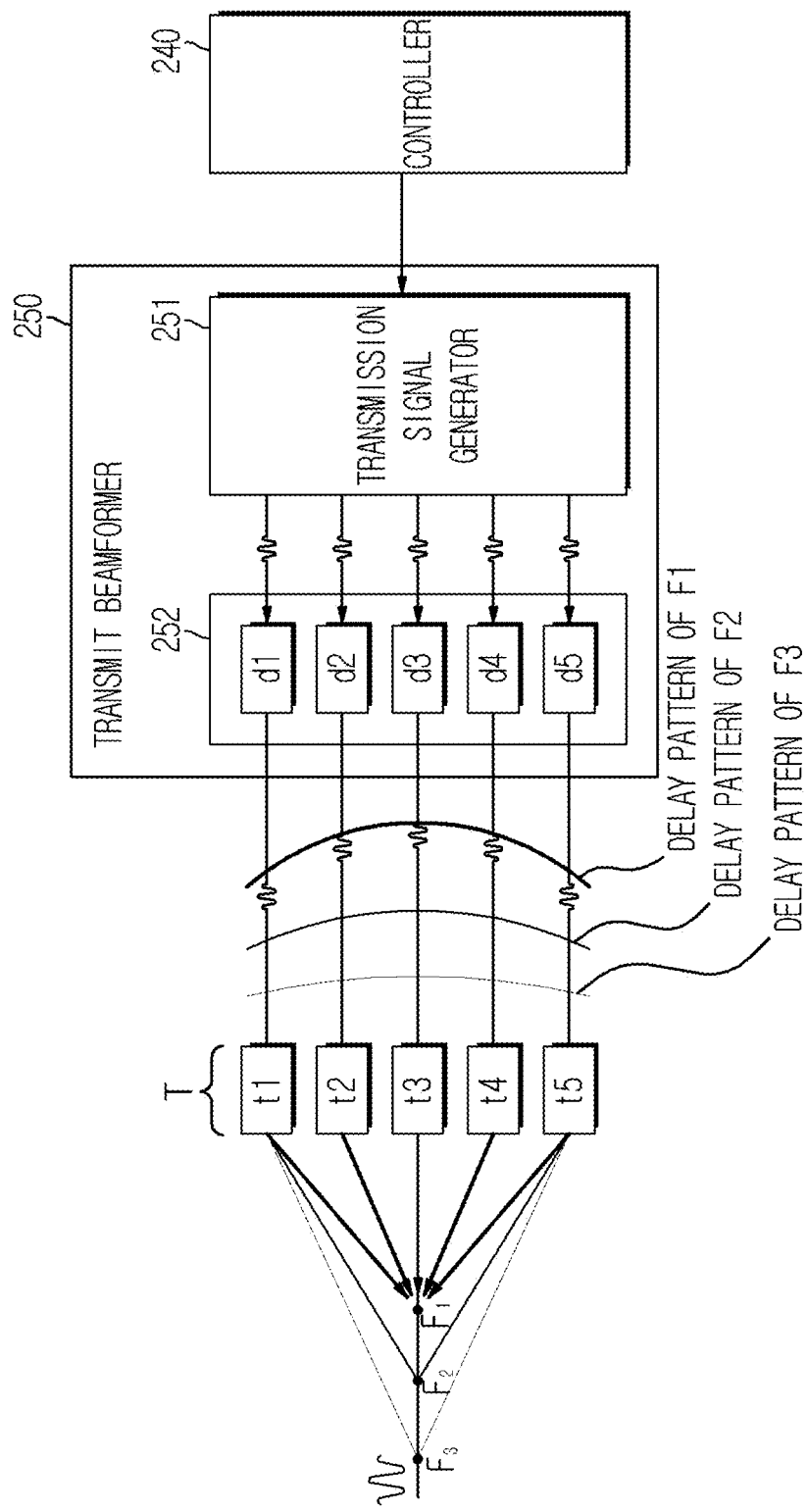
FIG. 3 is a block diagram of a transmit beamformer of an ultrasonic imaging apparatus.

FIG. 3 illustrates a configuration of the transmit beamformer 250. As illustrated in FIG. 3, the transmit beamformer 250 may include a transmission signal generator 251 and a time delay unit (also referred to herein as a "time delay device") 252.

The transmission signal generator 251 may generate transmission signals (i.e., high-frequency alternating current signals) that are to be applied to the ultrasonic elements T, according to a control signal from the controller 240. The transmission signals generated by the transmission signal generator 251 are provided to the time delay unit 252.

The time delay unit 252 may delay the transmission signals generated by the transmission signal generator 251 in order to adjust a time at which each transmission signal arrives at the corresponding ultrasonic element T. If the transmission signals delayed by the time delay unit 252 are applied to the ultrasonic elements T, the ultrasonic elements T generate ultrasonic waves corresponding to the frequencies of the transmission signals. The ultrasonic waves generated by the ultrasonic elements T are focused onto a focal point. The location of the focal point onto which the ultrasonic waves generated by the ultrasonic elements T are focused depends on what delay pattern has been applied to the transmission signals.

In more detail, in the exemplary embodiment illustrated in FIG. 3, five ultrasonic elements t1, t2, t3, t4, and t5 are provided, and three delay patterns that can be applied to transmission signals are represented as thick solid lines, medium solid lines, and thin solid lines, respectively.

When the delay pattern represented as the thick solid lines is applied to transmission signals generated by the transmission signal generator 251, ultrasonic waves generated by the ultrasonic elements t1 to t5 are focused onto a first focal point $F_1$.

When the delay pattern represented as the medium solid lines is applied to transmission signals generated by the transmission signal generator 251, ultrasonic waves generated by the ultrasonic elements t1 to t5 are focused onto a second focal point $F_2$ which is more distant than the first focal point $F_1$.

When the delay pattern represented as the thin solid lines is applied to transmission signals generated by the transmission signal generator 251, ultrasonic waves generated by the ultrasonic elements t1 to t5 are focused onto third focal point $F_3$ which is more distant than the second focal point $F_2$.

As described above, the location of a focal point varies according to what type of delay pattern is applied to transmission signals generated by the transmission signal generator 251. Accordingly, when a delay pattern is applied, ultrasonic waves that are to be applied to an object are focused onto a fixed focal point (fixed-focusing). However, when two or more different delay patterns are applied, ultrasonic waves that are to be applied to an object are focused onto several focal points (multi-focusing).

As such, ultrasonic waves generated by the individual ultrasonic elements T are fixed-focused onto a single focal point, or multi-focused onto several focal points. The focused ultrasonic waves are directed to the inside of an object. The ultrasonic waves directed to the inside of the object are reflected from a target area of the object. At least one ultrasonic echo reflected from the target area is received by the ultrasonic elements T. Then, the ultrasonic elements T convert the received ultrasonic echo into electrical signals. Hereinafter, the converted electrical signals will be simply referred to as ultrasonic signals. The ultrasonic signals output from the ultrasonic elements T are amplified and filtered, then converted into digital signals, and provided to the receive beamformer 260.

Referring again to FIG. 2, the receive beamformer 260 may perform receive beamforming on the ultrasonic signals converted into the digital signals. The receive beamforming is performed in order to correct time differences between ultrasonic signals output from individual ultrasonic elements and then to focus the corrected signals. The receive beamforming will be described in more detail with reference to FIG. 4, below.

Figure 4:
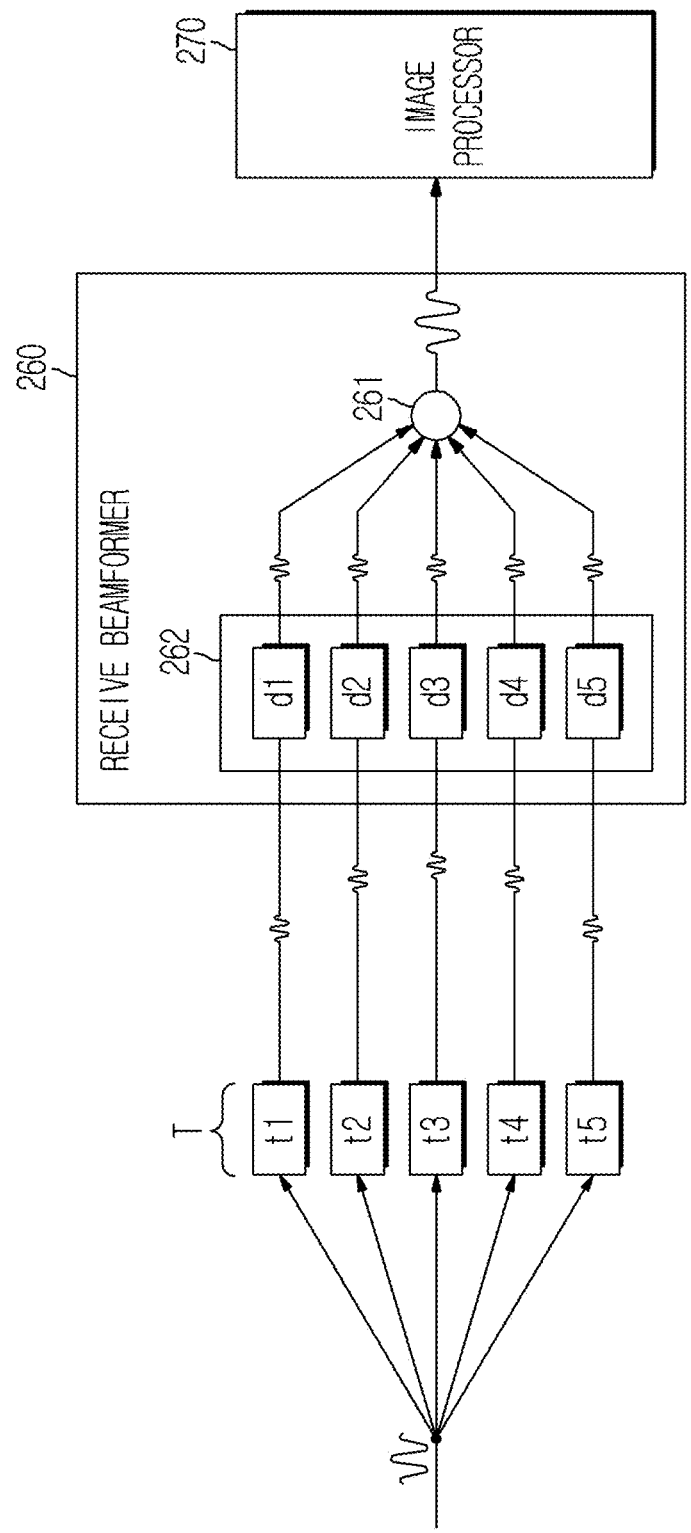
FIG. 4 is a block diagram of a receive beamformer of an ultrasonic imaging apparatus.

FIG. 4 is a block diagram of the receive beamformer 260, according to an exemplary embodiment. Referring to FIG. 4, the receive beamformer 260 may include a time-difference corrector 262 and a focusing unit (also referred to herein as a "focuser") 261.

The time-difference corrector 262 delays ultrasonic signals from the individual ultrasonic elements T by respective predetermined time periods so that the ultrasonic signals can be transferred to the focusing unit 261 at the same time.

The focusing unit 261 may focus the ultrasonic signals subject to time-difference correction by the time-difference corrector 262. At this time, the focusing unit 261 may focus the ultrasonic signals after allocating a predetermined weight (for example, a beamforming coefficient) to each ultrasonic signal in order to enhance or attenuate the corresponding ultrasonic signal rather than the other ultrasonic signals. The focused ultrasonic signal can be understood as a section image of the object 10. A plurality of section images may be acquired, and the acquired section images may be provided to the image processor 270.

Referring again to FIG. 2, the storage unit 280 may store data and algorithms needed to operate the ultrasonic imaging apparatus 20, and data generated by the ultrasonic imaging apparatus 20.

For example, the storage unit 280 may store a 2D color map. The 2D color map is a lookup table in which colors that are to be mapped to a 3D black-and-white ultrasonic image are arranged on a 2D coordinate system. The 2D color map may be generated based on at least one sample image which relates to a target inside the object 10. For example, the target may be a fetus, and a sample image about the fetus may be a baby's face image. That is, a 2D color map which relates to a fetus may be generated based on at least one baby's face image. Meanwhile, since a fetus's skin color depends on the fetus's race, a 2D color map may be generated for each race. Accordingly, a plurality of 2D color maps may be generated and classified according to races, and then stored in the storage unit 280.

In order to create a 2D color map, first, a color space of at least one sample image may be converted from a RGB color space to a YCbCr color space. This operation is performed in order to convert Red (R), Green (G), and Blue (B) values of each pixel of the sample image into Y, Cb, and Cr values. In the YCbCr color space, Y represents a luma component, Cb represents a blue-difference chroma component, and Cr represents a red-difference chroma component.

If conversion into the YCbCr color space is completed, each pixel of the sample image has Y, Cb, and Cr values. Then, a color gamut of the sample image may be modeled.

In order to model the color gamut of the sample image, the Y, Cb, and Cr values of each pixel of the sample image may be represented in the YCbCr space. Then, all values represented in the YCbCr color space may be projected onto a CbCr plane so as to obtain a Cb—Cr graph. The Cb—Cr graph may be divided into four quadrants, and a quadrant in which the projected values are distributed may depend on a kind of the sample image. For example, if the sample image is a baby's face image, the projected values are mainly distributed in the second quadrant of the Cb—Cr graph. If the sample image is an organ image acquired by photographing the organ, the projected values may be distributed in another one of the four quadrants of the Cb—Cr graph.

After the Cb—Cr graph is acquired, a color gamut of the sample image may be set based on the Cb—Cr graph. A boundary including all values projected onto the Cb—Cr plane may be set. For example, a hexagon boundary which includes all values projected onto the Cb—Cr plane may be set. A shape of the boundary may have been decided in advance, and is not limited to a hexagon. If a boundary is set, values of blank points on the boundary may be determined by using interpolation.

Figure 5:
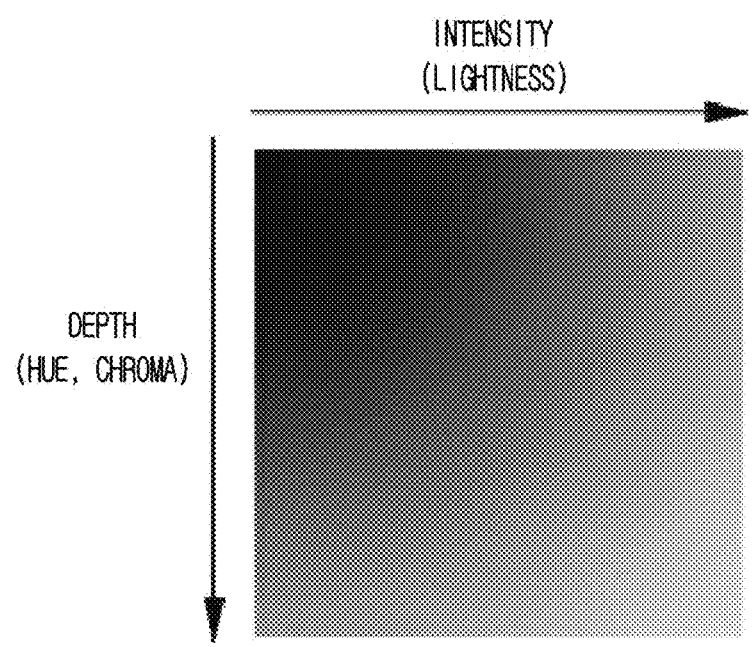
FIG. 5 shows an example of a two-dimensional (2D) color map.

If modeling of a color gamut is completed as described above, lightness, chroma, and hue values which correspond to the modeled color gamut may be calculated. Then, the lightness, chroma, and hue values may be mapped to 2D coordinates, thereby generating a 2D color map. In detail, lightness values are mapped to vary along the horizontal axis of the 2D coordinates, and chroma and hue values are mapped to vary along the vertical axis of the 2D coordinates. Here, a direction in which lightness values vary may correspond to a direction in which intensity values of a 3D black-and-while ultrasonic image vary, and a direction in which chroma and hue values vary may correspond to a direction in which depth values of the 3D black-and-while ultrasonic image vary. FIG. 5 shows a 2D color map in which lightness values are mapped to increase along the horizontal axis, and chroma and hue values are mapped to increase along the vertical axis.

The above description relates to a case of generating a 2D color map by mapping lightness to vary along the horizontal axis and mapping chroma and hue to vary along the vertical axis. However, a method of mapping lightness, chroma, and hue is not limited to this. For example, a 2D color map may be generated by mapping hue to vary along the horizontal axis, and mapping lightness and chroma to vary along the vertical axis. As another example, a 2D color map may be created by mapping chroma to vary along the horizontal axis, and mapping lightness and hue to vary along the vertical axis.

Meanwhile, in order to apply the 2D color map of FIG. 5 to a 3D black-and-white ultrasonic image, it is necessary to convert values of each respective pair of coordinates of the 2D color map into values in a color space which are usable in the corresponding imaging system. For example, lightness, chroma, and hue values of each pair of coordinates of the 2D color map may be converted into R, G, and B values. To do this, lightness, chroma, and hue values of each pair of coordinates of the 2D color map are converted into Y, Cb, and Cr values, and then, converted into R, G, and B values. In this way, each coordinate pair of the 2D color can be represented by R, G, and B values.

Referring again to FIG. 2, the storage unit 280 may store the 2D color map which is generated by the method as described above. That is, the storage unit 280 may store the 2D color map having coordinate pairs represented by R, G, and B values. As described above, if a target is a fetus, the storage unit 280 may store a 2D color map for each race. If a user inputs information about a race via the input unit 210, a 2D color map which corresponds to the input race information may be selected. The selected 2D color map may be used to produce a 3D color ultrasonic image of the target.

In addition, the storage unit 280 may store at least one of an algorithm which is usable for converting a color space of a sample image, an algorithm which is usable for performing color gamut modeling on a sample image, an algorithm for generating a 2D color map based on the modeled color gamut, and an algorithm for performing volume rendering. Also, the storage unit 280 may store ultrasonic images acquired by the image processor 270 which will be described below.

Figure 6:
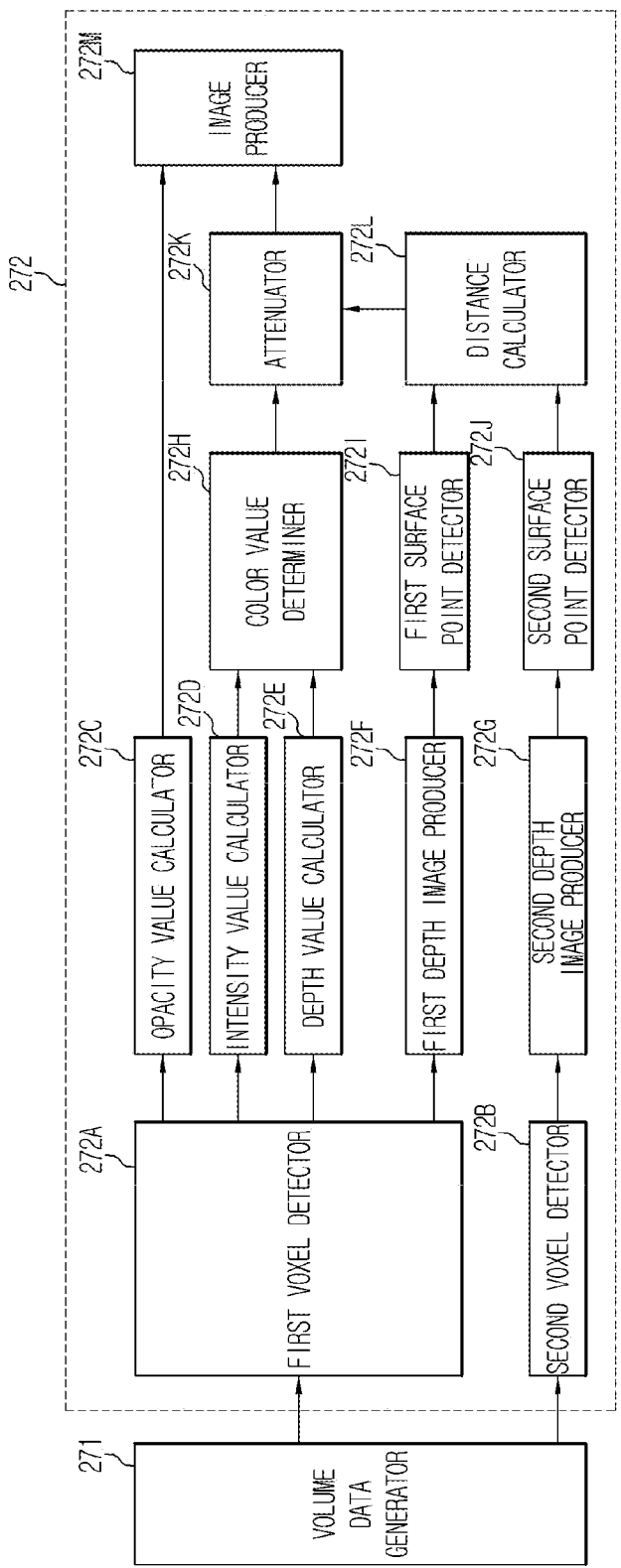
FIG. 6 is a block diagram of an image processor of an ultrasonic imaging apparatus.

The imaging processor 270 may include a volume data generator 271 and a volume rendering unit (also referred to herein as a "volume renderer") 272, as illustrated in FIG. 6.

The volume data generator 271 may produce an ultrasonic image based on ultrasonic signals focused by the receive beamformer 260. For example, if ultrasonic signals for a frame have been focused by the receive beamformer 260, an ultrasonic image may be produced. If ultrasonic signals for a plurality of frames have been focused by the receive beamformer 260, a plurality of ultrasonic images may be produced. Here, the plurality of ultrasonic images can be understood as volume data of the object 10.

The volume rendering unit 272 may perform volume rendering on the volume data. The volume rendering unit 272 may perform volume rendering by using any one or more of well-known volume rendering methods. In detail, the volume rendering may be classified into surface rendering and direct volume rendering.

The surface rendering is performed in order to extract surface information from volume data based on predetermined scalar values and amounts of spatial changes, to convert the surface information into a geometric factor, such as a polygon or a curved patch, and then to apply a conventional rendering technique to the geometric factor. Examples of the surface rendering are a marching cubes algorithm and a dividing cubes algorithm.

The direct volume rendering is performed in order to directly render volume data without converting volume data into a geometric factor. The direct volume rendering is useful to represent a translucent structure, because it can visualize the inside of an object as it is. The direct volume rendering may be classified into an object-order method and an image-order method, according to a way of approaching volume data.

The object-order method entails searching for 2D slices (that is, objects) in order under an assumption that volume data is composed of a stack of 2D slices, thereby determining pixel values.

The image-order method entails sequentially determining pixel values in the order of scan lines of an image. An example of the image-order method is Ray-Casting. The Ray-Casting will be briefly described with reference to FIG. 7, below.

Figure 7:
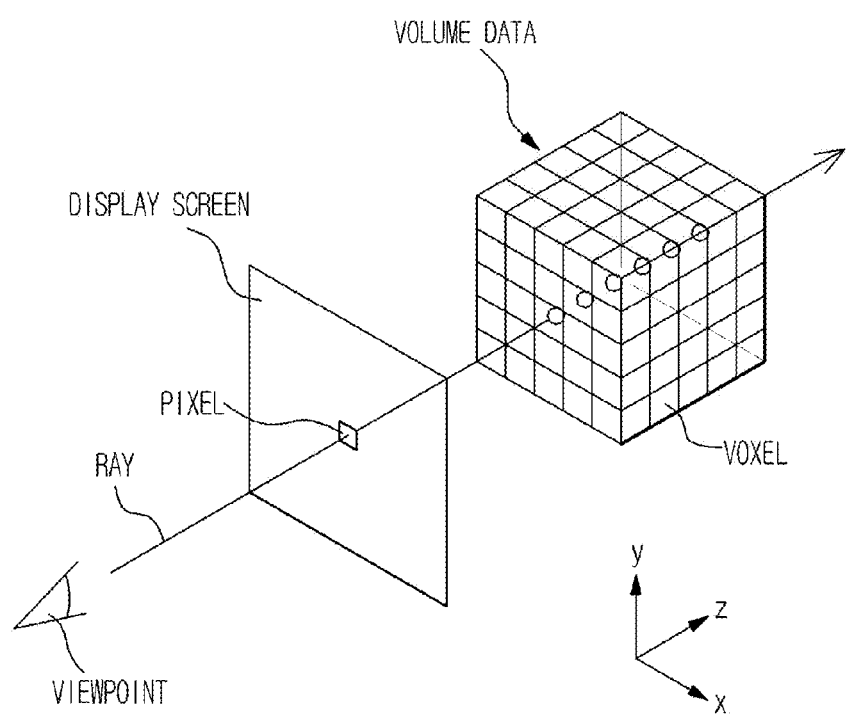
FIG. 7 is a view which illustrates a concept of volume rendering.

The Ray-Casting is performed, as illustrated in FIG. 7, in order to irradiate a virtual ray from a user's viewpoint toward a predetermined pixel of a display screen, and to detect voxels through which the virtual ray has propagated from among voxels of volume data. Then, intensity values of the detected voxels are accumulated in order to determine an intensity value of the corresponding pixel of the display screen, and opacity values of the detected voxels are accumulated in order to determine an opacity value of the corresponding pixel. The operation is performed on all pixels of the display screen, thereby obtaining a projection image which results from projecting the volume data onto the display screen.

Referring again to FIG. 6, the volume rendering unit 272 may perform volume rendering by using any one or more of the above-mentioned volume rendering methods. In the following description, a case in which the Ray-Casting is applied will be described as an example. If volume rendering is completed, a black-and-white projection image or a color projection image may be acquired based on a user's viewpoint. A kind of an image that is to be acquired by volume rendering may be determined based on a user's selection. A kind of an image that is to be acquired by volume rendering may be selected before ultrasonic diagnosis starts, and the selected value may be changed during ultrasonic diagnosis. In the following description, a case in which a color projection image is acquired will be described as an example.

According to an exemplary embodiment, the volume rendering unit 272 may generate a shadow map based on information about virtual light, and perform volume rendering by using the shadow map. The information about virtual light may include information about a position of the virtual light and a model of the virtual light. The shadow map is obtained by irradiating virtual light toward an object in an image to acquire a shadow of the object according to a shape of the object, rendering the shadow of the object to acquire texture, and mapping the texture to an image of the object.

According to an exemplary embodiment, the volume rendering unit 272 may perform translucent volume rendering. The translucent volume rendering is a rendering method by which a translucent projection image of an object can be acquired according to a relationship between a user's viewpoint and a position of virtual light. In the case of a human's skin which is translucent, when real light is irradiated onto the rear part of a human body, a skin part located close to the real light is shown to be translucent, since a part of the light penetrates the skin part, and a skin part located distant from the real light is shown to be opaque. The translucent volume rendering is performed in order to acquire a projection image in which areas located distant from virtual light are represented to be dark and areas located close to the virtual light are represented to be translucent by volume-rendering volume data in consideration of information about the virtual light. The translucent volume rendering will be briefly described as follows.

The volume rendering unit 272 may receive information about a user's viewpoint and a position of virtual light. The information about the user's viewpoint and the position of the virtual light may be received from a user via the input unit 210. For example, the user may input a numeral which corresponds to information about the user's viewpoint and a numeral which corresponds to information about a position of virtual light, by using a keyboard. As another example, the user may locate a pointer at a specific location of a display, and then select the pointer, thereby inputting information about the user's viewpoint or information about the position of virtual light. As another example, the user may touch or press a specific location of a display by using his/her finger or a stylus pen, thereby inputting information about the user's viewpoint or information about the position of virtual light.

Thereafter, the volume rendering unit 272 may produce depth images based on the user's viewpoint and the position of the virtual light. Hereinafter, the depth image produced based on the user's viewpoint is referred to as a "first depth image", and the depth image produced based on the position of the virtual light is referred to as a "second depth image".

Then, the volume rendering unit 272 may detect first surface points from the first depth image, and second surface points from the second depth image. The first surface points represent surface points that are shown from the user's viewpoint from among surface points which constitute the surface of the volume data, and the second surface points represent surface points that are shown from the position of the virtual light from among the surface points which constitute the surface of the volume data.

If the first and second surface points are detected, the volume rendering unit 272 may calculate respective distances between the first surface points and the second surface points. Then, color values of individual pixels of the projection image obtained based on the user's viewpoint may be determined based on the calculated distances. Hereinafter, a configuration of the volume rendering unit 272 may be described in more detail with reference to FIGS. 6, 7, 8, 9A, 9B, and 10.

As illustrated in FIG. 6, the volume rendering unit 272 may include a first voxel detector 272A, a second voxel detector 272B, an opacity value calculator 272C, an intensity value calculator 272D, a depth value calculator 272E, a first depth image producer 272F, a second depth image producer 272G, a color value determiner 272H, a first surface point detector 272I, a second surface point detector 272J, a distance calculator 272L, an attenuator 272K, and an image producer 272M.

Figure 8:
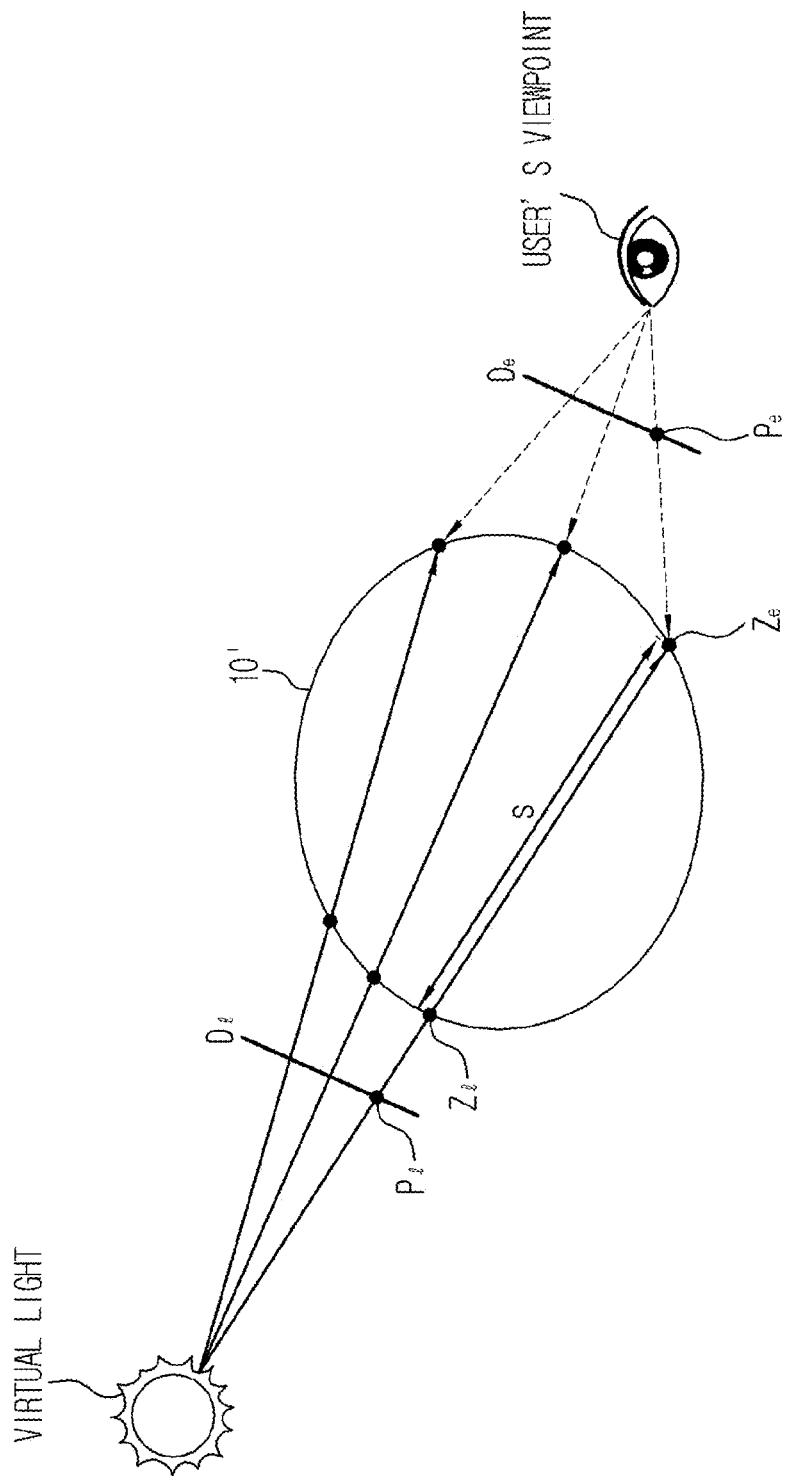
FIG. 8 is a plan view which illustrates a first surface point detected based on a position of a user's viewpoint and a second surface point detected based on a position of virtual light.

As illustrated in FIG. 8, the first voxel detector 272A may irradiate a first ray toward a predetermined pixel $P_e$ of a first plane $D_e$ from a user's viewpoint, and detect voxels through which the first ray has propagated from among voxels which constitute volume data 10'. The voxels through which the first ray has propagated from among the voxels which constitute the volume data 10' are referred to as "first voxels".

The opacity value calculator 272C may calculate opacity values from the voxel values of the first voxels. More specifically, the opacity value calculator 272C may calculate opacity values by applying an Opacity Transfer Function (OTF) to the voxel values of the first voxels. The OTF is a function which entails assigning a high opacity to voxels which correspond to tissue of interest, and a low opacity to voxels which correspond to the remaining tissue.

Although not shown in the drawings, the OTF may be implemented in any one or more of various ways. For example, the OTF may be implemented in a way of assigning an opacity of zero (0) to voxels having intensity values smaller than a threshold value, and assigning an opacity of one (1) to voxels having intensity values equal to or greater than the threshold value. Also, the OTF may be implemented in the form of a ramp function having threshold values of several stages, a square function, a trapezoid function, or a Gaussian function. Which way of the OTF is to be applied to the voxel values of the first voxels may be determined by an input value which is received from a user in advance, and the input value may be changed during diagnosis. For example, if a target is a fetus, the OTF may be implemented in a way of giving high opacity to voxels which correspond to skin tissue and low opacity to voxels which correspond to bones or organs.

The intensity value calculator 272D may calculate intensity values based on information about virtual light from the voxel values of the first voxels. More specifically, the intensity value calculator 272D may increase voxel values (that is, intensity values) of the first voxels located close to virtual light. Also, the intensity value calculator 272D may increase voxel values of the first voxels located distant from the virtual light by a lesser amount than an amount of increase of the voxel values of the first voxels located close to the virtual light, or maintain the voxel values of the first voxels located distant from the virtual light. The intensity values may be calculated for all of the first voxels. The intensity values of the first voxels may be provided to the color value determiner 272H which will be described below.

The depth value calculator 272E may calculate depth values of the first voxels. The depth values of the first voxels may be depth values of the first voxels from the user's viewpoint or from the origin in a 3D space in which volume data 10' is represented. The depth values of the first voxels may be calculated for all of the first voxels. The depth values of the first voxels may be provided to the color value determiner 272H which will be described below.

The color value determiner 272H may receive the intensity values of the first voxels from the intensity value calculator 272D, and receive the depth values of the first voxels from the depth value calculator 272H. Then, the color value determiner 272H may determine color values of all the first voxels with reference to a 2D color map. More specifically, the color value determiner 272H may search for coordinate values which respectively correspond to the intensity values of the first voxels in the horizontal axis of the 2D color map, and coordinate values which correspond to the depth values of the first voxels in the vertical axis of the 2D color map. Then, the color value determiner 272H may determine R, G, and B values assigned to the found coordinate values as color values of the first voxels. The color value determiner 272H may determine color values of all the first voxels in the same manner.

Figure 9A:
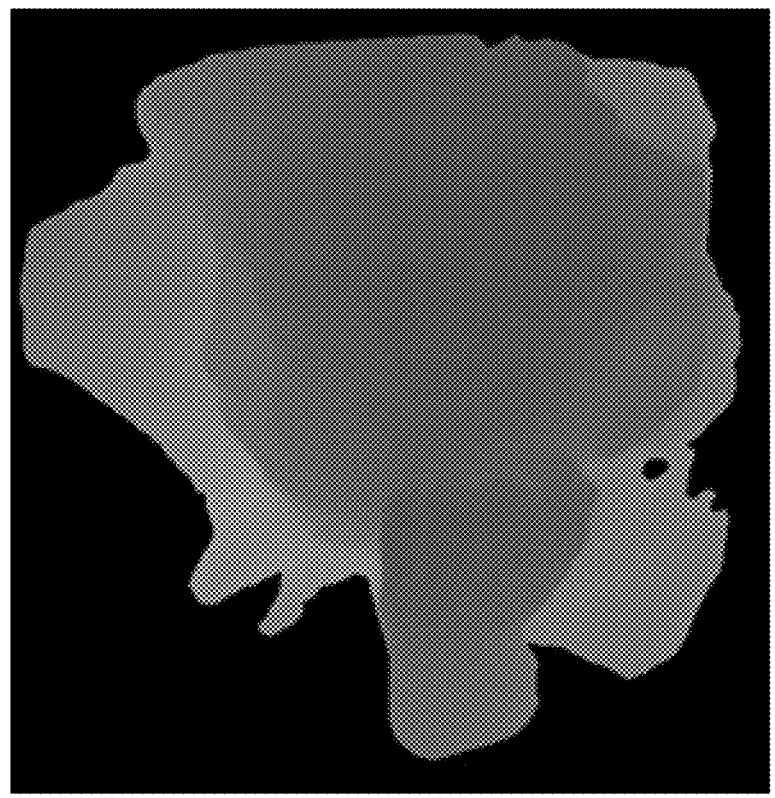
FIG. 9A shows an example of a first depth image produced based on a position of a user's viewpoint.

Referring to FIGS. 6 and 8, the first depth image producer 272M may irradiate a ray toward a pixel of the first plane $D_e$ from the user's viewpoint, and determine a distance from the pixel to a point for which an opacity value is identical to a predetermined threshold value, for example, 0.5, as a depth value of the pixel. If the operation is performed on all the pixels of the first plane $D_e$, and a depth value determined for each pixel is represented in gray scale, a first depth image as illustrated in FIG. 9A may be obtained.

The second surface point detector 272I may detect first surface points from the first depth image. As described above, the first surface points represent surface points that are shown from the user's viewpoint from among points which constitute the surface of the volume data 10'.

Figure 9B:
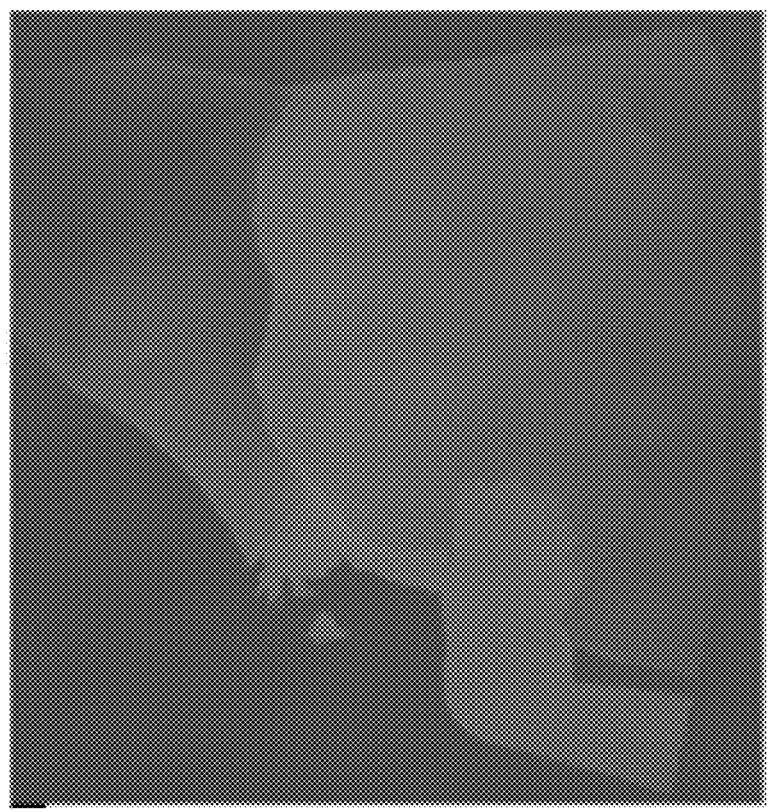
FIG. 9B shows an example of a second depth image produced based on a position of virtual light.

Referring to FIGS. 6 and 8, the second depth image producer 272G may irradiate a ray toward a pixel of a second plane $D_l$ from the position of virtual light, and determine a distance from the pixel to a point for which an opacity value is identical to a predetermined threshold value, for example, 0.5, as a depth value of the pixel. If the operation is performed on all the pixels of the second plane $D_l$, and a depth value determined for each pixel is represented in gray scale, a second depth image as illustrated in FIG. 9B may be obtained.

The second surface point detector 272J may detect second surface points from the second depth image. As described above, the second surface points represent surface points that are shown from the position of the virtual light from among the points which constitute the surface of the volume data 10'.

The distance calculator 272L may calculate respective distances between the first surface points and the second surface points. For example, as illustrated in FIG. 8, if the first plane $D_e$ faces the second plane $D_l$, a distance S between a first surface point $Z_e$ at which a first ray emitted from a first pixel $P_e$ of the first plane $D_e$ meets the surface of an object 10', and a second surface point $Z_l$ at which a second ray emitted from a second pixel $P_l$ at a location on the second plane $D_l$ which corresponds to the first pixel $P_e$ of the first plane $D_e$ meets the surface of the object 10' can be calculated. The distance S between the first surface point $Z_e$ and the second surface point $Z_l$ may be calculated by applying Equation 1, below.

$$S = |Z_l - Z_e| \qquad \text{[Equation 1]}$$

In Equation 1, $Z_l$ represents the second surface point, $Z_e$ represents the first surface point, and S represents a distance between the first surface point $Z_e$ and the second surface point $Z_l$. The calculated distance values may be provided to the attenuator 272K.

The attenuator 272K may receive the color values of the first voxels from the color value determiner 272H. Also, the attenuator 272K may receive the distance values between the first surface points and the second surface points from the distance calculator 272L. Then, the attenuator 272K may apply an attenuation coefficient to the color value of at least one first voxel from among the color values of the first voxels.

For example, the attenuator 272K may apply an attenuation coefficient to each of the color values of all the first voxels. As another example, the attenuator 272K may apply an attenuation coefficient only to the color values of the first voxels which correspond to the first surface points among the first voxels. The first voxels to which the attenuation coefficient is to be applied among the first voxels may be selected by a user.

According to an exemplary embodiment, the attenuator 272K may apply different respective attenuation coefficients to each of the R, G, and B values of the first voxels. The attenuation coefficients that are respectively applied to the R, G, and B values may be expressed as Equation 2, below.

$$col\_r' = col\_r \times \exp(-s^{a_r}) \times \lambda_r$$

$$col\_g' = col\_g \times \exp(-s^{a_g}) \times \lambda_g$$

$$col\_b' = col\_b \times \exp(-s^{a_b}) \times \lambda_b \quad \text{[Equation 2]}$$

In Equation 2, col_r, col_g, and col_b represent input values for R, G, and B values. In particular, col_r, col_g, and col_b represent R, G, and B values when no attenuation coefficient is applied thereto. That is, col_r, col_g, and col_b are R, G, and B values received from the color value determiner 272H. col_r', col_g', and col_b' represent output values for R, G, and B values. That is, col_r', col_g', and col_b' represent R, G, and B values after an attenuation coefficient is applied thereto. S represents a distance between the first surface point and the second surface point, calculated by the distance calculator 272L. $a_r$, $a_g$, and $a_b$ represent gradient correction factors of exponential function curves for R, G, and B values. The gradient correction factors of the exponential function curves may be set to, for example, $a_r=1.2$, $a_g=1.5$, and $a_b=1.5$. Also, $\lambda_r$, $\lambda_g$, and $\lambda_b$ represent scaling coefficients for R, G, and B values. The scaling coefficients may be set to, for example, $\lambda_r=1.0$, $\lambda_g=0.9$, and $\lambda_b=0.9$.

As seen from Equation 2, as a distance between the first surface point and the second surface point increases, a greater attenuation coefficient is applied to color values. As such, by making color values of a first voxel which corresponds to the first surface point increasingly attenuate as a distance between the first surface point and the second surface point increases, an influence of virtual light with respect to the first surface point can be represented.

In detail, as a first surface point is located more distant from virtual light, the first surface point is less influenced by light irradiated from the virtual light, and as a first surface point is located closer to the virtual light, the first surface point is more influenced by light irradiated from the virtual light. Accordingly, by making color values of a first voxel which corresponds to a first surface point increasingly attenuate as a distance between the first surface point and the corresponding second surface point increases, a pixel which corresponds to a first surface point located distant from virtual light is represented with a dark color, and a pixel which corresponds to a first surface point located close to virtual light is represented with a bright color. As a result, an object can have a translucent effect according to a position of virtual light.

Figure 10:
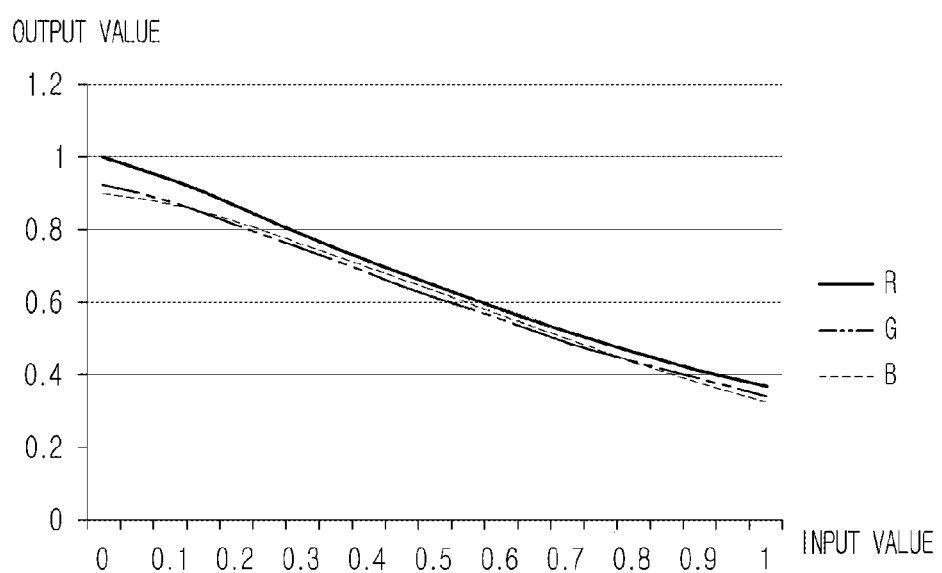
FIG. 10 illustrates graphs which show relationships between input values and output values of Red (R), Green (G), and Blue (B) values of a first voxel.

FIG. 10 illustrates graphs which show relationships between input values and output values of R, G, and B values. Referring to FIG. 10, the graphs corresponding to the R, G, and B values start at different points. Start points of the individual graphs depend on respective values of scaling coefficients $\lambda_r$, $\lambda_g$, and $\lambda_b$. As such, by differentiating the start points of the individual graphs, color values which are capable of representing colors more similar to a human's skin colors can be obtained.

Further, the color values output from the attenuator 272K may be provided to the image producer 272M. The color values output from the attenuator 272K may be color values to which an attenuation coefficient has been applied. Alternatively, the color values output from the attenuator 272K may include color values to which an attenuation coefficient has been applied and color values to which no attenuation coefficient has been applied.

The image producer 272M may accumulate the color values of the first voxels received from the attenuator 272K, and determine the accumulated color value as a final color value of the pixel onto which the first ray has been irradiated. Also, the image producer 272M may accumulate the opacity values of the first voxels received from the opacity value calculator 272C, and determine the accumulated opacity value as a final opacity value of the pixel onto which the first ray has been irradiated. The color values of the first voxels may be accumulated by applying Equation 3, below. Also, the opacity values of the first voxels may be accumulated by applying Equation 4, below.

$$\hat{C}_i = (1 - \hat{\alpha}_{i-1})C_i + \hat{C}_{i-1} \quad \text{[Equation 3]}$$

$$\hat{\alpha}_i = (1 - \hat{\alpha}_{i-1})\alpha_i + \hat{\alpha}_{i-1} \quad \text{[Equation 4]}$$

In Equations 3 and 4, $C_i$ represents a color value of an i-th first voxel, and $\alpha_i$ an opacity value of the i-th first voxel. $\hat{C}_{i-1}$ represents a color value accumulated until an (i−1)-th first voxel, and $\hat{C}_i$ represents a color value accumulated until an i-th first voxel. $\hat{\alpha}_{i-1}$ represents an opacity value accumulated until the (i−1)-th first voxel, and $\hat{\alpha}_i$ represents an opacity value accumulated until the i-th first voxel.

The above description with reference to FIG. 8 relates to a case of irradiating a ray toward a predetermined pixel of the first plane $D_e$, but a plurality of rays may be respectively irradiated toward all pixels of the first plane $D_e$. If an accumulation of color values and opacity values with respect to all the pixels of the first plane $D_e$ is completed, a projection image subject to volume rendering with respect to the user's viewpoint may be obtained.

As described above, by determining the color values of the first voxels with reference to the 2D color map, and applying the attenuation coefficient according to the distances between the first surface points and the second surface points to at least one of the determined color values, a projection image of an object that is shown to be translucent according to a position of virtual light can be obtained.

Figure 11A:
FIG. 11A shows an example of a projection image obtained through translucent volume rendering when a user's viewpoint and virtual light are located in front of an object.
Figure 11B:
FIG. 11B shows an example of a projection image obtained through translucent volume rendering when a user's viewpoint is located in front of an object and virtual light is located to the right of the user's viewpoint.

FIGS. 11A and 11B show projection images which may be obtained as the results of translucent volume rendering. FIG. 11A shows an example of a projection image obtained by performing translucent volume rendering when a user's viewpoint and virtual light are located in front of an object, and FIG. 11B shows an example of a projection image obtained by performing translucent volume rendering when a user's viewpoint is located in front of an object and virtual light is located to the right of the user's viewpoint. Referring to FIG. 11B, surface parts of an object, located relatively close to virtual light, are represented with a bright color, and surface parts of the object, located relatively distant from the virtual light, are represented with a dark color. Also, referring to FIG. 11B, some parts of a fetus's skin are shown to be translucent according to the position of the virtual light.

Meanwhile, the above-described exemplary embodiment relates to a case of determining color values of first voxels with reference to a 2D color map, applying an attenuation coefficient to at least one of the color values, and accumulating the color values to which the attenuation coefficient has been applied. However, the present disclosure is not limited to this exemplary embodiment. Although not shown in the drawings, the color values of the first voxels may be determined with reference to the 2D color map, the determined color values may be all accumulated, and then the attenuation coefficient may be applied to the accumulated color values.

Figure 12:
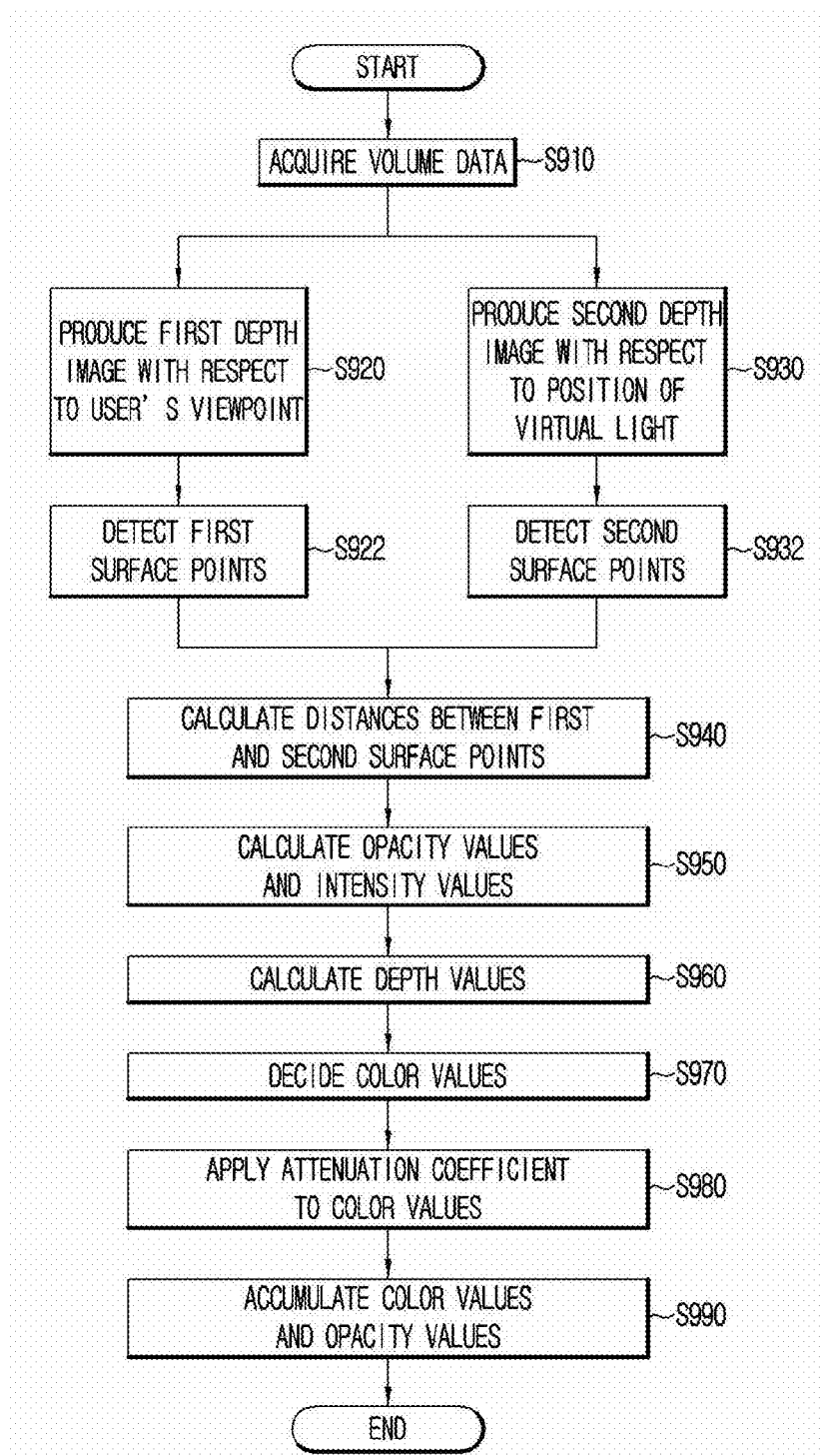
FIG. 12 is a flowchart which illustrates an image processing method, according to an exemplary embodiment.

FIG. 12 is a flowchart which illustrates an image processing method, according to an exemplary embodiment.

Referring to FIGS. 2, 6, and 12, first, volume data which relates to the object 10 may be acquired, in operation S910. At this time, information about a user's viewpoint and a position of virtual light may be input via the input unit 210.

Thereafter, in operation S920, a first depth image may be produced with respect to the user's viewpoint. More specifically, referring to FIG. 8, a first ray may be irradiated toward the pixel $P_e$ of the first plane $D_e$ from a user's viewpoint, and a distance from the pixel $P_e$ to a point for which an opacity value is identical to a predetermined threshold value, for example, 0.5, may be determined as a depth value of the pixel $P_e$. By performing the operation on all the pixels of the first plane $D_e$, a first depth image may be produced.

If a first depth image is produced, first surface points may be detected from the first depth image, in operation S922. The first surface points are surface points that are shown from the user's viewpoint from among surface points which constitute the surface of the volume data 10'.

Meanwhile, a second depth image may be produced with respect to the position of the virtual light, in operation S930. More specifically, referring to FIG. 8, a ray may be irradiated toward the pixel $P_l$ of the second plane $D_l$ from a position of virtual light, and a distance from the pixel $P_l$ to a point for which an opacity value is identical to a predetermined threshold value, for example, 0.5, may be determined as a depth value of the pixel $P_l$. By performing the operation on all the pixels of the second plane $D_l$, a second depth image may be produced.

If a second depth image is produced, second surface surfaces may be detected from the second depth image, in operation 932. The second surface points are surface points that are shown from the position of the virtual light from among surface points which constitute the surface of the volume data 10'.

If the first and second surface points are detected, respective distances between the first and second surface points may be calculated, in operation S940. More specifically, referring to FIG. 8, a distance S between a first surface point $Z_e$ and a second surface point $Z_l$ of pixels which correspond to the same position on the first and second depth images may be calculated. The distance S between the first surface point $Z_e$ and the second surface point $Z_l$ may be calculated by applying Equation 1. Distances between the first and second surface points may be calculated with respect to all the pixels on the first and second depth images.

Thereafter, first voxels through which the first ray irradiated toward the first pixel $P_e$ of the first plane $D_e$ has propagated may be detected.

If the first voxels are detected, opacity values and intensity values may be calculated based on voxel values of the detected first voxels, in operation S950. The opacity values of the first voxels may be calculated by applying the OTF to the first voxels. The intensity values of the first voxels may be calculated based on the position of the virtual light and/or model information of the virtual light.

Further, depth values of the first voxels may be calculated, in operation S960.

Thereafter, color values of the first voxels may be determined based on the intensity values and depth values of the first voxels, and a 2D color map, in operation S970. More specifically, operation S970 may include operations of: searching for a coordinate which corresponds to the intensity value of a first voxel in the horizontal axis of the 2D color map; searching for a coordinate which corresponds to the depth value of the first voxel in the vertical axis of the 2D color map; determining R, G, and B values which correspond to the found coordinates as color values of the first voxel; and performing the operation on all the first voxels.

If color values of all the first voxels are determined based on the 2D color map, an attenuation coefficient may be applied to at least one of the determined color values, in operation S980. For example, an attenuation coefficient may be applied to all of the determined color values. As another example, an attenuation coefficient may be applied only to color values of a first voxel which corresponds to a first surface point from among the determined color values. Also, different respective attenuation coefficients may be applied to each of R, G, and B colors. The attenuation coefficients that are respectively applied to the R, G, and B values may be represented as Equation 2 expressed above.

After an attenuation coefficient is applied to color values of at least one first voxel, color values and opacity values of the first voxels may be accumulated, in operation S990. The accumulated color values correspond to color values of the pixel $P_e$ onto which the first ray has been irradiated. The accumulated opacity value corresponds to an opacity value of the pixel $P_e$ onto which the first ray has been irradiated.

Operations S950 to S990 are performed on all the pixels of the first plane $D_e$, so that a projection image of the object 10 that is shown to be translucent according to a position of virtual light can be obtained.

The projection image of the object 10 may be displayed via the display unit 220.

Some components of the above-described exemplary embodiments may be implemented as a "module". Here, the term "module" refers to a software component or a hardware component, such as a Field Programmable Gate Array (FPGA) or Application Specific Integrated Circuit (ASIC), which performs certain tasks. However, the module is not limited to software or hardware. A module may advantageously be configured to reside on the addressable storage medium/media and configured to execute one or more processors.

Thus, a module may include, by way of example, one or more components, such as software components, object-oriented software components, class components and task components, processes, functions, attributes, procedures, subroutines, segments of program code, drivers, firmware, microcode, circuitry, data, databases, data structures, tables, arrays, and variables. The functionality provided for in the components or modules may be combined into fewer components or modules or may be further separated into additional components or modules. Further, the components or modules can operate at least one processor (e.g., a central processing unit (CPU)) provided in a device.

Some exemplary embodiments can also be embodied as a medium (e.g., a computer readable medium) which includes a computer readable code/instruction for controlling at least one processing component of the above-described exemplary embodiments. The computer readable medium can correspond to medium/media that can store and/or transmit the computer readable code.

The computer readable code can be recorded in medium and transmitted over the Internet. Examples of the computer readable medium include read-only memory (ROM), random-access memory (RAM), CD-ROMs, magnetic tapes, floppy disks, optical data storage devices, and carrier waves (such as data transmission through the Internet). Also, the medium may be a non-transitory computer-readable medium. The computer readable medium can also be distributed over network coupled computer systems so that the computer readable code is stored and executed in a distributed fashion. Further, for example, the processing component can include a processor or a computer processor, and can be distributed and/or included in a device.

Although a few exemplary embodiments have been shown and described, it will be appreciated by those skilled in the art that changes may be made in these exemplary embodiments without departing from the principles and spirit of the present disclosure, the scope of which is defined in the claims and their equivalents.

What is claimed is:

1. An image processing apparatus comprising:
a volume data generator configured to generate volume data which relates to an object;
a volume renderer configured to project the volume data to a first plane with respect to a viewpoint of a user, and to acquire a projection image,
wherein the volume renderer is further configured to determine a value of each pixel of the projection image based on respective distances between first surface points and second surface points, the first surface points being points that are shown from the viewpoint of the user from among points which constitute a surface of the volume data, and the second surface points being points that are shown from a position of virtual light from among the points which constitute the surface of the volume data.

2. The image processing apparatus according to claim 1, wherein the volume renderer comprises:
a first voxel detector configured to detect a plurality of first voxels through which a first ray which is irradiated toward a pixel of the first plane from the viewpoint of the user has propagated, from among voxels which constitute the volume data;
a color value determiner configured to determine respective color values of the first voxels based on a two-dimensional (2D) color map; and
an attenuator configured to apply an attenuation coefficient based on the respective distances between the first surface points and the second surface points to at least one color value of the color values of the first voxels.

3. The image processing apparatus according to claim 2, wherein
the 2D color map is generated based on a color gamut of a sample image of the object,
lightness values of the color gamut of the sample image are mapped to vary along a horizontal axis of the 2D color map;
chroma values and hue values of the color gamut of the sample image are mapped to vary along a vertical axis of the 2D color map; and
the mapped lightness values, the mapped chroma values, and the mapped hue values are respectively converted into Red (R), Green (G), and Blue (B) values, and then stored.

4. The image processing apparatus according to claim 3, wherein the color value determiner is further configured to search for coordinate values which correspond to intensity values of the first voxels in the horizontal axis of the 2D color map, to search for coordinate values which correspond to depth values of the first voxels in the vertical axis of the 2D color map, and to determine R, G, and B values which correspond to the found coordinate values as respective color values of the first voxels.

5. The image processing apparatus according to claim 2, wherein the color values of the first voxels include Red (R), Green (G), and Blue (B) values, and the attenuator is further configured to apply different respective attenuation coefficients to each of the R, G, and B values.

6. The image processing apparatus according to claim 2, wherein the volume renderer further comprises an image producer configured to determine a value which is obtained by accumulating color values to which the attenuation coefficient has been applied from among the color values of the first voxels and color values to which the attenuation coefficient has not been applied from among the color values of the first voxels, as a color value of the pixel of the first plane.

7. The image processing apparatus according to claim 1, wherein the volume renderer comprises an image producer configured to determine a value which is obtained by accumulating opacity values of the first voxels, as an opacity value of the pixel of the first plane.

8. The image processing apparatus according to claim 1, further comprising a display device configured to display the projection image.

9. An image processing method comprising:
generating volume data which relates to an object; and
projecting the volume data to a first plane with respect to a viewpoint of a user, and acquiring a projection image,
wherein the acquiring the projection image comprises determining a value of each pixel of the projection image based on respective distances between first surface points and second surface points, the first surface points being points that are shown from the viewpoint of the user from among points which constitute a surface of the volume data, the second surface points being points that are shown from a position of virtual light from among the points which constitute the surface of the volume data.

10. The image processing method according to claim 9, wherein the acquiring the projection image comprises:
detecting first voxels through which a first ray which is irradiated toward a pixel of the first plane from the viewpoint of the user has propagated, from among voxels which constitute the volume data;
determining respective color values of the first voxels based on a two-dimensional (2D) color map; and
applying an attenuation coefficient based on the respective distances between the first surface points and the second surface points to at least one color value of the color values of the first voxels.

11. The image processing method according to claim 10, wherein
the 2D color map is generated based on a color gamut of a sample image of the object,
lightness values of the color gamut of the sample image are mapped to vary along a horizontal axis of the 2D color map;
chroma values and hue values of the color gamut of the sample image are mapped to vary along a vertical axis of the 2D color map; and
the mapped lightness values, the mapped chroma values, and the mapped hue values are respectively converted into Red (R), Green (G), and Blue (B) values, and then stored.

12. The image processing method according to claim 11, wherein the determining the color values of the first voxels comprises:
- searching for coordinate values which correspond to intensity values of the first voxels in the horizontal axis of the 2D color map;
- searching for coordinate values which correspond to depth values of the first voxels in the vertical axis of the 2D color map; and
- determining R, G, and B values which correspond to the found coordinate values as respective color values of the first voxels.

13. The image processing method according to claim 10, wherein the color values of the first voxels include Red (R), Green (G), and Blue (B) values, and the applying the attenuation coefficient comprises applying different respective attenuation coefficients to each of the R, G, and B values.

14. The image processing method according to claim 10, further comprising determining a value which is obtained by accumulating color values to which the attenuation coefficient has been applied from among the color values of the first voxels and color values to which the attenuation coefficient has not been applied from among the color values of the first voxels, as a color value of the pixel of the first plane.

15. The image processing method according to claim 9, further comprising determining a value which is obtained by accumulating opacity values of the first voxels, as an opacity value of the pixel of the first plane.

* * * * *